(12) United States Patent
Hitchcock et al.

(10) Patent No.: US 6,965,791 B1
(45) Date of Patent: Nov. 15, 2005

(54) IMPLANTABLE BIOSENSOR SYSTEM, APPARATUS AND METHOD

(75) Inventors: Robert W. Hitchcock, Sandy, UT (US); James L. Sorenson, Salt Lake City, UT (US)

(73) Assignee: Sorenson Medical, Inc., Salt Lake City, UT (US)

(*) Notice: Subject to any disclaimer, the term of this patent is extended or adjusted under 35 U.S.C. 154(b) by 148 days.

(21) Appl. No.: 10/401,224

(22) Filed: Mar. 26, 2003

(51) Int. Cl.$^7$ ............................................... A61B 5/05
(52) U.S. Cl. ...................... 600/345; 600/309; 600/347; 600/365; 204/403.01
(58) Field of Search ............................... 600/300, 309, 600/345–365, 372–381; 204/403.01–403.15, 204/406, 407, 433, 279, 280, 297.01

(56) References Cited

U.S. PATENT DOCUMENTS

| | | | |
|---|---|---|---|
| 4,561,963 A * | 12/1985 | Owen et al. ................. | 204/433 |
| 4,567,963 A * | 2/1986 | Sugimoto .................... | 182/236 |
| 4,703,756 A * | 11/1987 | Gough et al. ................ | 600/347 |
| 4,861,454 A * | 8/1989 | Ushizawa et al. ........... | 204/414 |
| 5,165,407 A * | 11/1992 | Wilson et al. ............... | 600/345 |
| 5,390,671 A | 2/1995 | Lord et al. | |
| 5,527,444 A * | 6/1996 | Sweeney, Jr. ................ | 204/415 |
| 5,568,806 A | 10/1996 | Cheney, II et al. | |
| 5,586,553 A | 12/1996 | Halili et al. | |
| 5,951,521 A | 9/1999 | Mastrototaro et al. | |
| 6,329,161 B1 | 12/2001 | Heller et al. | |
| 6,360,888 B1 * | 3/2002 | McIvor et al. ............... | 206/305 |
| 6,613,379 B2 * | 9/2003 | Ward et al. ................. | 427/2.11 |
| 2004/0254433 A1 * | 12/2004 | Bandis et al. ............... | 600/347 |

OTHER PUBLICATIONS

Teflon. Academic Press Dicitionary of Science and Technology (1992). http://www.xreferplus.com/entry/3166958.*
Brindra et al., Design and in Vitro Studies of a Needle-Type Ghucose Sensor for Subcutaneous Monitoring, Anal. Chem., 1991, pp. 1692-1696, vol. 63.
Churchouse et al., Needle Enzyme Electrodes for Biological Studies, Biosensors, 1986, pp. 325-342, vol. 2.
Matthews et al., An Amperometric Needle-type Glucose Sensor Tested in Rats and Man, Diabetic Medicine, 1988, pp. 248-252, vol. 5.
Moussy et al., Performance of Subcutaneously Implanted Needle-Type Glucose Sensors Employing a Novel Trilayer Coating, Anal. Chem, 1993, pp. 2072-2077, vol. 65.
Moussy et al., A miniaturized Nafion-based glucose sensor: in vitro and in vivo evaluation in dogs, The International Journal of Artificial Organs, 1994, pp. 88-94, vol. 17. No. 2.

* cited by examiner

Primary Examiner—Max F. Hindenburg
Assistant Examiner—Patricia Mallari
(74) Attorney, Agent, or Firm—TraskBritt

(57) ABSTRACT

An implantable biosensor assembly and system includes an enzymatic sensor probe from which subcutaneous and interstitial glucose levels may be inferred. The assembly may be associated by direct percutaneous connection with electronics, such as for signal amplification, sensor polarization, and data download, manipulation, display, and storage. The biosensor comprises a miniature probe characterized by lateral flexibility and tensile strength and has large electrode surface area for increased sensitivity. Irritation of tissues surrounding the probe is minimized due to ease of flexibility and small cross section of the sensor. Foreign body reaction is diminished due to a microscopically rough porous probe surface.

52 Claims, 12 Drawing Sheets

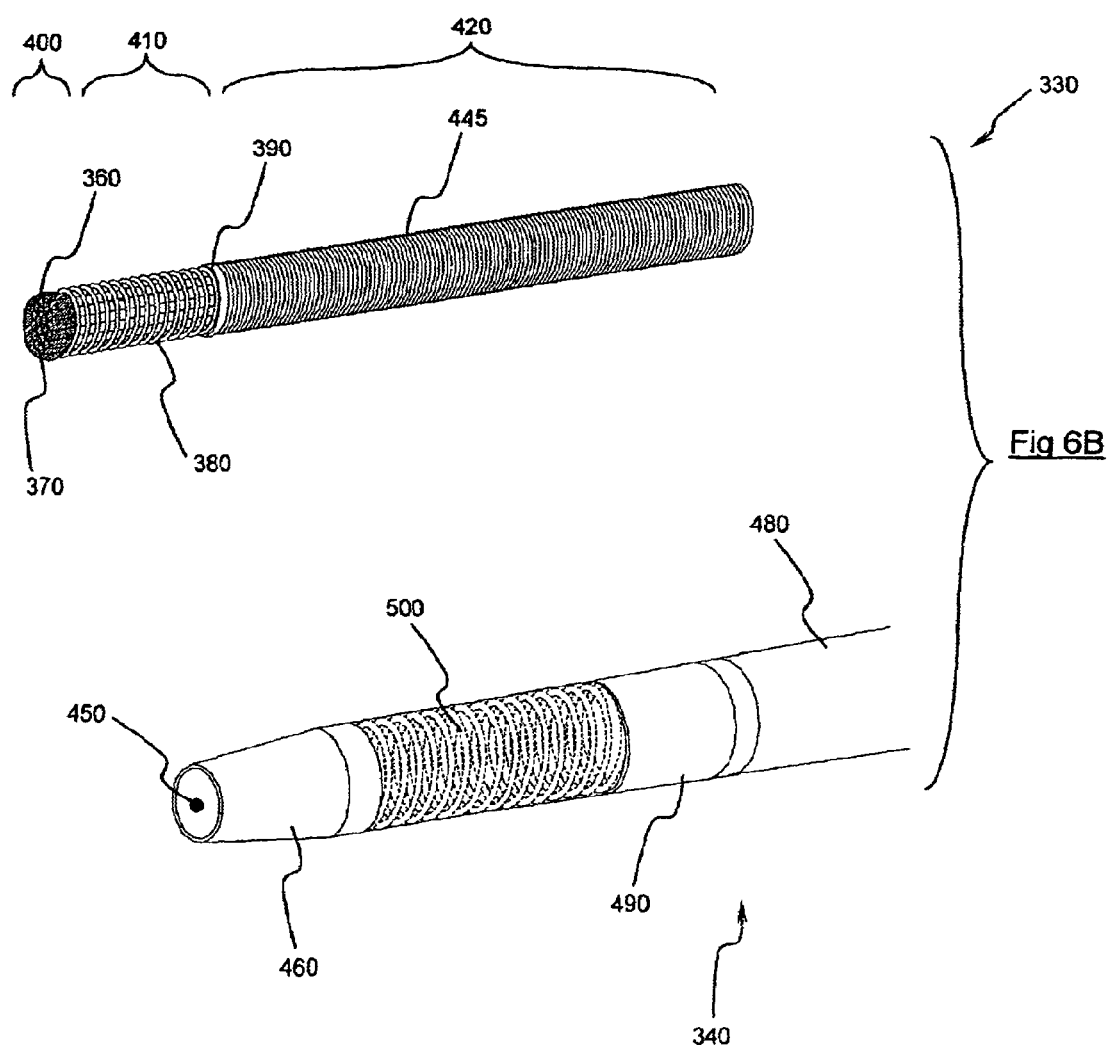

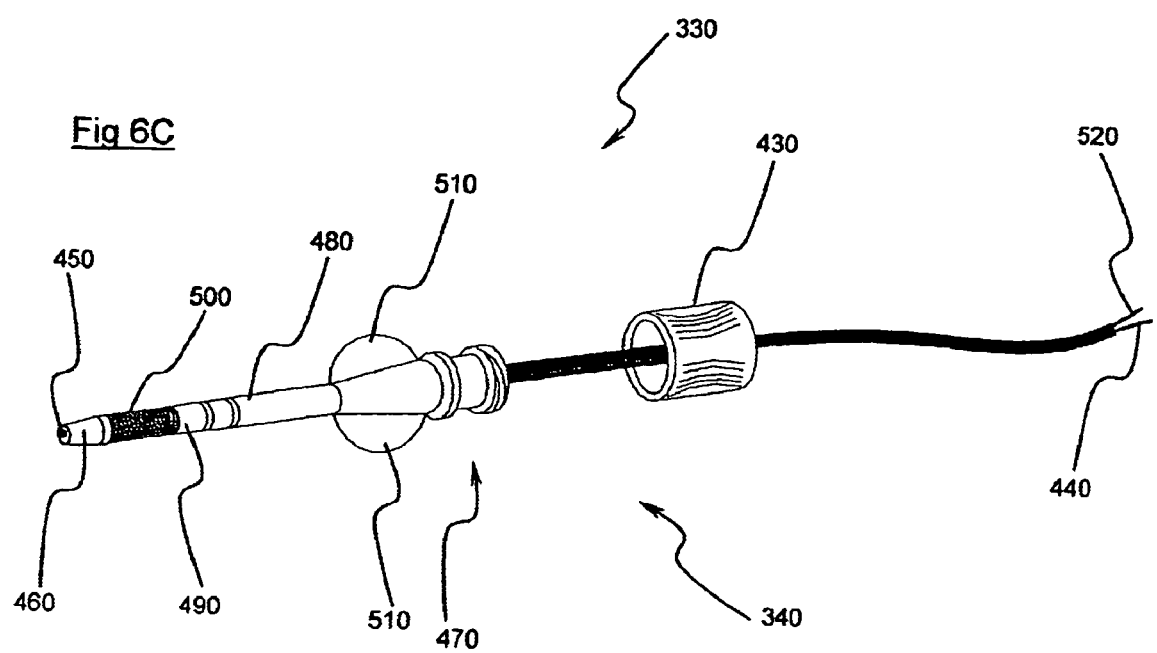

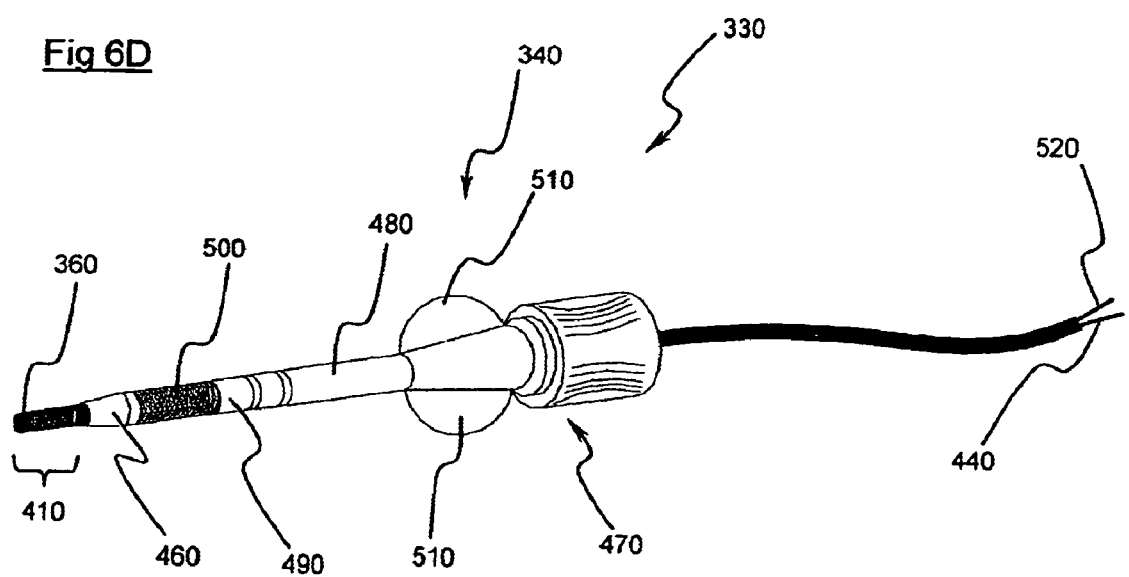

IMPLANTABLE BIOSENSOR SYSTEM, APPARATUS AND METHOD

TECHNICAL FIELD

This invention relates generally to medical devices and associated methods such as measuring glucose for ongoing diabetes management. The inventions described herein also be used for enzymatic determination of other analytes. This invention provides a particularly useful application for an implantable biosensor.

BACKGROUND

Heretofore, treatment and management of diabetes has been undertaken through many and varied techniques. Formerly, glucose in urine was measured, though recognized as less than adequate due to the time delay inherent in the metabolism and voiding process. Currently, the approach predominantly used for self- monitoring of blood glucose requires periodic pricks of the skin with a needle, whereby a blood sample is obtained and tested directly to provide information about blood glucose levels. This information is then utilized as a basis from which to schedule the administration of insulin to maintain glucose equilibrium within the patient. Direct measurement of glucose levels in periodic blood samples from diabetes patients provides reasonably useful information about insulin levels at certain selected points in time. However, the dynamic nature of blood glucose chemistry and the complexity of factors influencing blood sugar levels renders such periodic information less than optimal.

The glucose level in the subcutaneous interstitial fluid very closely approximates the glucose level in the blood, with a negligible time lag. The variables of patient food selection, physical activity and insulin dosage, regime and protocol for a person with diabetes each have a dynamic impact on physiologic balance within the patient's body that can change dramatically over a short period of time. If the net result of changes in these variables and dynamics results in disequilibrium expressed as too much glucose ("hyperglycemia"), then more insulin is required, whereas too little glucose ("hypoglycemia") requires immediate intervention to raise the glucose levels. A deleterious impact on physiology follows either such disequilibrium.

Hyperglycemia is the source of most of the long-term consequences of diabetes, such as blindness, nerve degeneration, and kidney failure. Hypoglycemia, on the other hand, poses the more serious short-term danger. Hypoglycemia can occur at any time of the day or night and can cause the patient to lose consciousness. Guarding against hypoglycemia may require frequent monitoring of blood glucose levels and render the skin-prick approach tedious, painful and in some cases impractical. Even diligent patients who perform finger-sticking procedures many times each day achieve only a poor approximation of continuous monitoring. Accordingly, extensive attention has been given to development of improved means of monitoring patient glucose levels for treatment of diabetes.

Many efforts to continuously monitor glucose levels have involved implantable electrochemical biosensors. These amperometric sensors utilize an immobilized form of the enzyme glucose oxidase to catalyze the conversion of oxygen and glucose to gluconic acid and hydrogen peroxide. Such sensors may be used to measure hydrogen peroxide resulting from the enzymatic reaction. Alternatively, these glucose oxidase based biosensors measure oxygen consumption to infer glucose concentrations.

Typical implantable, subcutaneous needle-type biosensors are disclosed in various publications, such as the following examples. An Amperometric Needle-type Glucose Sensor Tested in Rats and Man, by D. R. Matthews, E. Bown, T. W. Beck, E. Plotkin, L. Lock, E. Gosden, and M. Wickham discloses an amperometric glucose-measuring 25 gauge (0.5 mm diameter) needle-type sensor using a glucose oxidase and dimethyl ferrocene paste behind a semi-permeable membrane situated over a window in the needle. Performance of Subcutaneously Implanted Needle-Type Glucose Sensors Employing a Novel Trilayer Coating, by Francis Moussy, D. Jed Harrison, Darryl W. O'Brien, and Ray V. Rajotte teaches a miniature, needle-type glucose sensor utilizing a perfluorinated ionomer, Nafion, as a protective, biocompatible, outer coating, and poly (o-phenylenediamine) as an inner coating to reduce interference by small, electroactive compounds. Glucose oxidase immobilized in a bovine serum albumin matrix was sandwiched between these coatings. The entire assembly of Pt working electrode and Ag/AgCl reference electrode was 0.5 mm in diameter and could be inserted subcutaneously through an 18-gauge needle. Needle Enzyme Electrodes for Biological Studies by S. J. Churchouse, C. M. Battersby, W. H. Mullen and P. M. Vadgama presents yet another needle enzyme electrode characterized as the most promising approach to miniaturization for invasive use. A Miniaturized Nafion-based Glucose Sensor by F. Moussy, D. J. Harrison, and R. V. Rajotte, while teaching a high sensitivity (due in part to greater surface area of the electrode) needle-type sensor with a spear-shaped point, acknowledges the need for more protection against abrasion. Design and In Vitro Studies of a Needle-Type Glucose Sensor for Subcutaneous Monitoring by Dilbir S. Bindra, Yanan Zhang, George S. Wilson, Robert Sternberg, Daniel R. Thevenot, Dinah Moatti and Gerard Reach sets forth yet another needle-type glucose microsensor having a 26-gauge (0.45-mm) outside diameter.

Additional needle-type implantable biosensors are disclosed in certain United States patent documents. Relevant documents include: "Subcutaneous Glucose Electrode" to Heller et al., U.S. Pat. No. 6,329,161 B1; "Subcutaneous Implantable Sensor Set Having The Capability To Remove Deliver Fluids To An Insertion Site" to Mastrototaro et al., U.S. Pat. No. 5,951,521; "Transcutaneous Sensor Insertion Set" to Halili et al., U.S. Pat. No. 5,586,553; "Transcutaneous Sensor Insertion Set" to Cheney, II et al., U.S. Pat. No. 5,568,806; "Transcutaneous Sensor Insertion Set" to Lord et. al., U.S. Pat. No. 5,390,671; and "Implantable Glucose Sensor" to Wilson et al., U.S. Pat. No. 5,165,407.

To provide continuous measurement, biosensors can be placed for extended periods of time in various locations within the body. One method of placement is percutaneously with an indwelling sensor having an attached external wire associated with a readout device. A risk of infection is associated with percutaneous biosensors, and they must typically be replaced at regular intervals because of the risk of infection at the insertion site.

Another problem with implanted sensors is irritation of the tissues surrounding the implanted biosensors. Such irritation is typically due, in part, to the lateral rigidity of prior art biosensors. Related to this problem is the scarring of surrounding tissue due not only to rigidity but also to abrupt edges associated with the implants. Scar tissue surrounding reference electrodes of the prior art is not desirable, but may be tolerated in some cases. However, scar tissue can be materially detrimental to the sensor function in the vicinity of the working electrode because it impedes the diffusion of oxygen and glucose.

Further, to protect itself against a perceived invader, the body commonly experiences a foreign body reaction by encapsulating the implanted biosensors with protein, which may shorten the life of the implant and adversely affect the accuracy of information provided. The size of the sensor may also be regarded as a problem; smaller is better for comfort. Further yet, interfering compounds, such as for example, ascorbic acid, and acetaminophen, can reduce the accuracy of prior art amperometric glucose sensors given the membranes selected historically to envelope such sensors. Additionally the quantity of dissolved oxygen is limited at high glucose concentrations thus leading to non-linear output of sensor signals at high glucose concentrations.

A need remains for a sensor including a miniaturized probe of suitable materials and characteristics that may facilely be placed percutaneously. A need exists for a miniaturized, albeit durable, implantable biosensor percutaneously deployable wherein irritation to tissues surrounding the biosensor is minimized. A need also exists to achieve a rough exterior of the portion of an implantable biosensor exposed to surrounding tissue so that foreign body reaction may reduced. Similarly, there is a need for a selected membrane or membrane combination suitable to correction of non-linear diffusion of glucose. Further needed is a method of manufacturing such a miniaturized yet strong and durable implantable biosensor with resilient flexibility and minimal surface relief while achieving a microscopically porous surface.

BRIEF SUMMARY OF THE INVENTION

The invention includes an implantable needle-type biosensor wherein an electric signal is produced between first and second electrical contacts responsive to an electrochemical reaction in a body. A needle-like probe element is typically inserted through an introducer cannula into tissues of a subject's body. An implantable needle element of an exemplary biosensor includes an elongate core having a distal end spaced apart axially from a proximal end. A workable core may be formed as a single element, or may include a plurality of axially oriented fibers arranged in a bundle. Certain cores are nonconductive to electric current. Workable cores may be made from natural and synthetic fibers, metal, polymers, and plastics. Currently preferred cores are made from polymer material.

In general, a working electrode is associated with a distal end of the core. Desirably, the working electrode is arranged to protrude, beyond a distal end of an introducer cannula, into intimate contact with tissue of a subject's body. A reference electrode is included in a biosensor to produce an electrical signal, in combination with the working electrode, responsive to the electrochemical reaction. Structure included in a biosensor is adapted to resist direct physical contact between the working electrode and the reference electrode to prevent forming a direct electrical short between those electrodes.

A first electrically conductive path exists between the working electrode and a first electrical contact. Similarly, a second electrically conductive path exists between the reference electrode and a second electrical contact. The first and second electrical contacts typically are associated with a hub operable to secure a probe in relation to a cannula. A signal may be received from the first and second contacts for data reduction and correlation to a physiological state in a body, such as glucose concentration. In general, the signal is transmitted through a sensor cable affixed to structure of the hub. A workable sensor cable includes first and second wires, each wire having a first end arranged to make respective electrical connections with one of the first or second electrical contacts, and a second end of each wire typically being affixed to a sensor module operable to impose a conditioning signal on the biosensor probe.

A working electrode can include a metal element (usually including platinum) formed as a wrap about a portion of the core. An exemplary working electrode includes a length of a first wire arranged to circumscribe a plurality of revolutions about the core. In such an exemplary working electrode, a diameter of the first wire is between about 0.001 and about 0.005 inches. Desirably, the first wire is arranged to form a spiral path. Usually, at least a portion of the core is disposed substantially coaxial with an axis of the spiral. A currently preferred spiral path has an axial spacing, between the centerlines of a pair of adjacent wire wraps, sized between about one and about two diameters of the first wire. A larger spacing, up to about five diameters (or even more in some cases), is also workable, although it is recognized that the electrode's active surface area decreases with larger pitch spacing. Typically, the working electrode is arranged to reinforce the core so as to enable a reinforced core to carry an axial compression load permitting insertion of a distal tip of the biosensor through an introducer catheter for placement of the working electrode into intimate contact with tissue of the subject's body.

The reference electrode typically includes a metal element (usually including Silver, and preferably including chlorided Silver) and can also be associated with the distal end of a core. A reference electrode may alternatively be associated with an introducer cannula, or some other structure. In the latter case, a reference electrode may sometimes be recessed into an exterior surface of the introducer cannula. In any event, it is currently preferred for a reference electrode to be placed into intimate contact with tissue of a subject's body. One embodiment of a reference electrode includes a length of a second wire formed as a wrap about a portion of the core. Another embodiment of a reference electrode may be fashioned as a length of wire, wire coil, foil, film, or coating associated with a cannula.

A preferred electrode (either working or reference) may be characterized as having: an axially interrupted load path between first and second ends, a maximum equivalent outside diameter, a minimum equivalent inside diameter, and a surface texture disposed between the first and second ends that has a radially oriented component. Such an electrode has a larger reactive surface area and a lower bending stiffness compared to a hollow cylinder structured from an equivalent material and having equivalent maximum outside and minimum inside diameters.

The core of a biosensor probe according to the instant invention, can function to assist in retraction of the various components of the biosensor probe. One structure operable to assist in such retraction includes a plug carried on a distal end of the core. The plug can be structured as a stopper that is too large to pass through an electrode. Such a stopper operates to resist extraction of the core from within a portion of the working electrode as the biosensor is removed from the subject's body, so as not to leave a detached portion of the working electrode in the body. One functional plug is preferably formed, at least in part, with a polymer coating. Another functional plug can include a droplet of dielectric adhesive. A functional plug typically forms an enlargement in a cross-section of the core, with a portion of the enlargement being disposed distal to the working electrode.

In probes carrying both working and reference electrodes, a dielectric spacer is usually interposed between the electrodes to resist direct physical contact between them. A functional dielectric spacer can be made from a droplet of dielectric adhesive bonded to a portion of the core. Such a droplet desirably also is arranged as a stopper to resist extraction of the core from within a portion of the reference electrode as a biosensor is removed from a subject's body, so to not leave a detached portion of the reference electrode in the body.

A probe portion of a biosensor includes a sensor shaft disposed between the working electrode and the hub. The sensor shaft generally includes a cylinder disposed circumferentially about an axial length of the core proximal to the working electrode. A currently preferred cylinder includes a plurality of circumferential wrappings of a component wire having a smaller diameter than a diameter of the formed cylinder. Wrappings forming the cylinder desirably are closely spaced, or even touching, in an axial direction along an axis of the cylinder whereby to enable the shaft to carry an axial compression load effective to install the biosensor probe portion through an introducer cannula and into a body. Usually, a dielectric spacer is disposed at a distal end of the cylinder to resist direct physical contact between the shaft and an electrode. One such dielectric spacer can be formed from a droplet, or small quantity, of dielectric adhesive bonded to a portion of the core.

Desirably, an exterior coating of a negatively charged polymer is applied to the working electrode. One operable negatively charged polymer includes sulfonated polyethersulfone. It is also sometimes desirable to provide a microscopically roughed-up surface to the outer surface of the coating to enhance biocompatibility of the biosensor with tissue of the subject's body. Desirable surface texture is formed by elements having a size of between about 5 and 50 microns. Multifiber cores typically include a plurality of spaces between the fibers operable to carry glucose oxidase whereby to enhance a volume of glucose oxidase associated with a working electrode.

The instant invention may be embodied broadly as an implantable biosensor including an introducer cannula and a probe element. The introducer cannula includes a lumen extending axially between its proximal and distal ends. The cannula's proximal end carries affixing structure adapted to resist motion of the proximal end relative to a skin surface of a subject and either carries holding structure configured to receive a probe. A distal end of the cannula carries a first electrode. A probe includes an elongate core having a distal end spaced apart axially from a proximal end, and is structured for sliding installation, through the cannula lumen, into a subject. A proximal end of the probe is associated with a hub adapted to be held by the cannula holding structure. The distal end of the probe carries a second electrode. The probe and cannula are cooperatively structured on assembly to resist direct physical contact between the first electrode and the second electrode. Desirably, the first and second electrodes are installed to be in intimate contact with the tissue of a subject.

A method for manufacturing an implantable, needle-type biosensor probe with a transversely flexible first electrode effective to resist irritation at a site of implantation in a subject, includes the steps of: a) providing a core comprising a first nonconductive material; b) disposing a first electrode in a reinforcing path about the core; c) disposing a first electrical conductor between the first electrode and a hub associated with a proximal end of the probe; and d) disposing a second electrical conductor between a second electrode and the hub. The method can also include the step of: e) forming a stopper carried by the core, a portion of the stopper being disposed distal to the first electrode and operable to resist extraction of the core from within an interior of the electrode, whereby to retain an association between the core and the electrode to resist leaving a portion of the electrode in a subject subsequent to removal of the probe.

Sometimes, step b) includes: forming the first electrode as an axially interrupted first cylinder having a first length between a first end and a second end, a maximum equivalent outside diameter, and a minimum equivalent inside diameter. The first cylinder desirably includes a surface texture disposed between its first and second ends that has a radially oriented component so as to provide a larger reactive surface area and a lower bending stiffness than a second cylinder having an equivalent maximum outside diameter and first length. An exemplary electrode having such conformation can be formed from a wire of between about 0.001 and about 0.005 inches in diameter, with the wire being disposed to occupy a spiral path about the core.

In some cases, the method may further include disposing a second wire circumferentially about the core in a spiral reinforcing path operable to enhance an axial load carrying capability of the core, whereby to form the second electrode. Typically, the step of applying an insulation to a conductive path extending proximally from one or both electrodes is further included. When two electrodes are carried on a core, the method additionally can include affixing a dielectric element between the working and the reference electrodes. Such dielectric element desirably is also adapted to resist extraction of the core from retention in an electrode, whereby to resist leaving a portion of that electrode inside a subject subsequent to extraction of the probe. Generally, the method includes the step of wrapping, or otherwise disposing, a third wire circumferentially about the core in a spiral reinforcing path to form a shaft of the probe. Furthermore, the method includes affixing the hub to a proximal portion of the shaft.

Coatings are typically applied in additional steps subsequent to assembly of basic probe structure. An inner exclusion membrane is formed in a first coating step by applying a solution, such as 5% polyethersulfone, to the working electrode. A second coating step includes applying a solution, such as 1% glucose oxidase, 0.6% albumin and 0.0.5% glutaraldehyde, to the working electrode to form a middle enzymatic membrane. In a third coating step, a solution, such as 5% polyurethane is applied to both the working and the reference electrodes to form an outer polymer membrane. The final polyurethane coating desirably is microscopically roughed-up by performing a phase inversion polymerization procedure. In general, a workable phase version polymerization procedure includes immediately dipping the final polyurethane layer into a water bath to largely rinse away the miscible solvent soon after the first of the polymer molecules comprising the 5% solution have begun to bond with the second-to-last layer. Desirably, the resulting surface includes protruding particles sized between about 5 and 50 microns.

BRIEF DESCRIPTION OF THE SEVERAL VIEWS OF THE DRAWINGS

In the drawings, which illustrate what are currently regarded as the best modes for carrying out the invention:

FIG. 6B is an enlarged perspective view in elevation with greater resolution of a portion of the embodiment illustrated in FIG. 6A;

FIG. 6C is a perspective view in elevation of the embodiment of FIG. 6A in a partially assembled configuration; and FIG. 6D is a perspective view in elevation of the embodiment of FIG. 6A in an assembled configuration.

BEST MODE OF THE INVENTION

Figure 1:
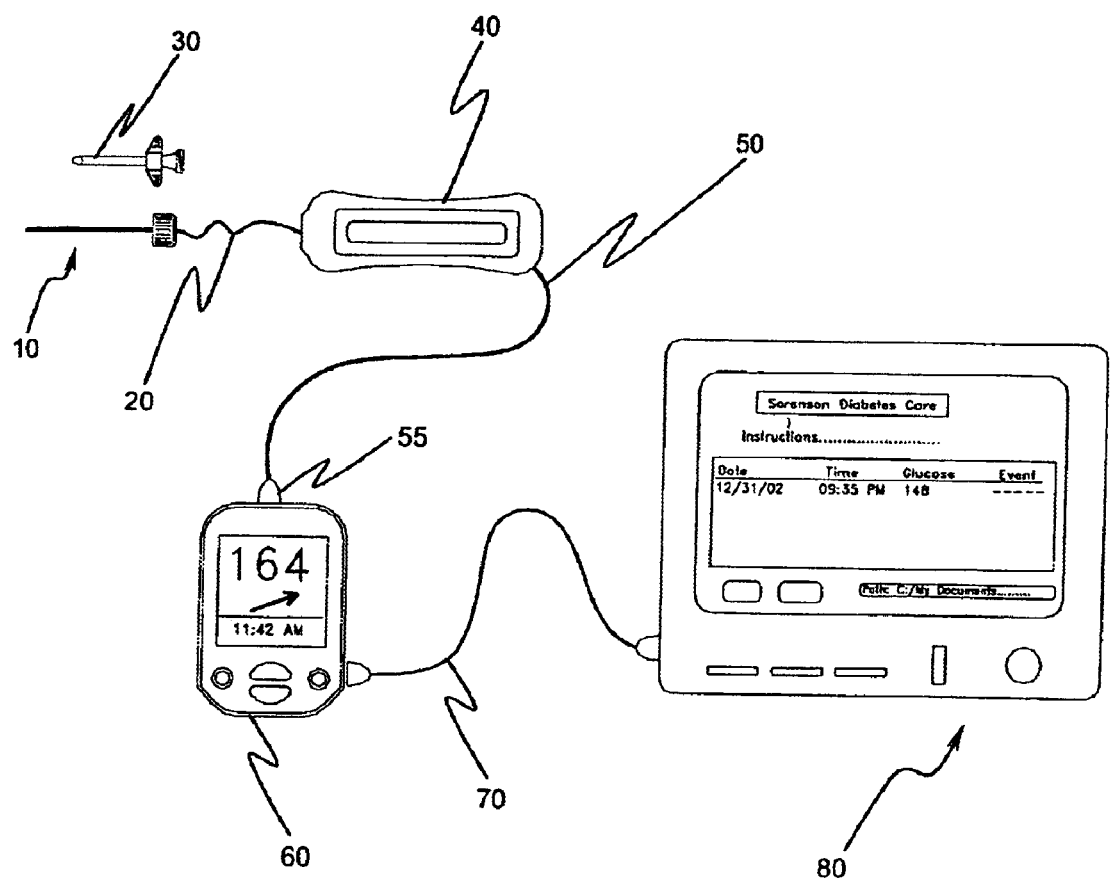
FIG. 1 is a schematic of one configuration of a preferred embodiment.

FIG. 1 illustrates a preferred embodiment in which an implantable biosensor, generally 10, and associated sensor cable 20 is provided. Miniaturized and highly flexible, the biosensor 10 may be placed into a subject subcutaneously through a cannula such as an introducer catheter 30. The biosensor 10 as illustrated is associated percutaneously through the sensor cable 20 with a sensor module 40 which in turn is associated via a module cable 50 with a Sensor Display Unit ("SDU") 60. The SDU 60 can be structured to be interactive across SDU cable 70 with computer hardware and other software, generally 80.

The foregoing biosensor system may include a single use portion and a reusable portion. The single use portion includes the introducer catheter 30, the biosensor 10, the sensor cable 20, the sensor module 40 and the module cable 50. The introducer catheter 30 can generally be regarded as a separate component, although certain embodiments may incorporate the catheter to carry a portion of a biosensor probe. The biosensor 10, sensor cable 20, sensor module 40 and module cable 50 desirably are all be permanently affixed to each other. Module cable 50 typically is removably attached at disconnect 55 to a sensor display unit (SDU) 60. The SDU 60 and SDU cable 70 may be reused. When attached to the SDU 60, the SDU cable 70 allows the glucose information to be downloaded to a personal computer 80 that is loaded with the sensor download software 80.

To install a preferred embodiment of a biosensor 10, introducer catheter 30 can be inserted into the subcutaneous tissue of a subject on a supporting needle (not illustrated). The supporting needle is removed to leave an opening through the cannula, and typically, a short path extension into the subject's tissue. Then, the biosensor 10 may be placed into the catheter 30 such that a portion of the biosensor 10 protrudes beyond the catheter 30. The working electrode 100 and reference electrode 110 of the presently preferred embodiment are designed to be deployed 3–10 nm into the subcutaneous fatty tissue of a subject to monitor glucose concentration in the interstitial fluids. The introducer catheter 30/biosensor 10 assembly, as well as the sensor module 40, are then generally affixed to the skin (not shown) via an adhesive patch.

The biosensor 10 produces a small electrical current that is proportional to the glucose concentration. This current is amplified and conditioned by the sensor module 40. The sensor module 40 also provides a polarization voltage to the working electrode of the biosensor 10. The amplified signal typically is interpreted by the SDU 60, which generally calibrates, displays and stores the glucose data.

Figure 2A:
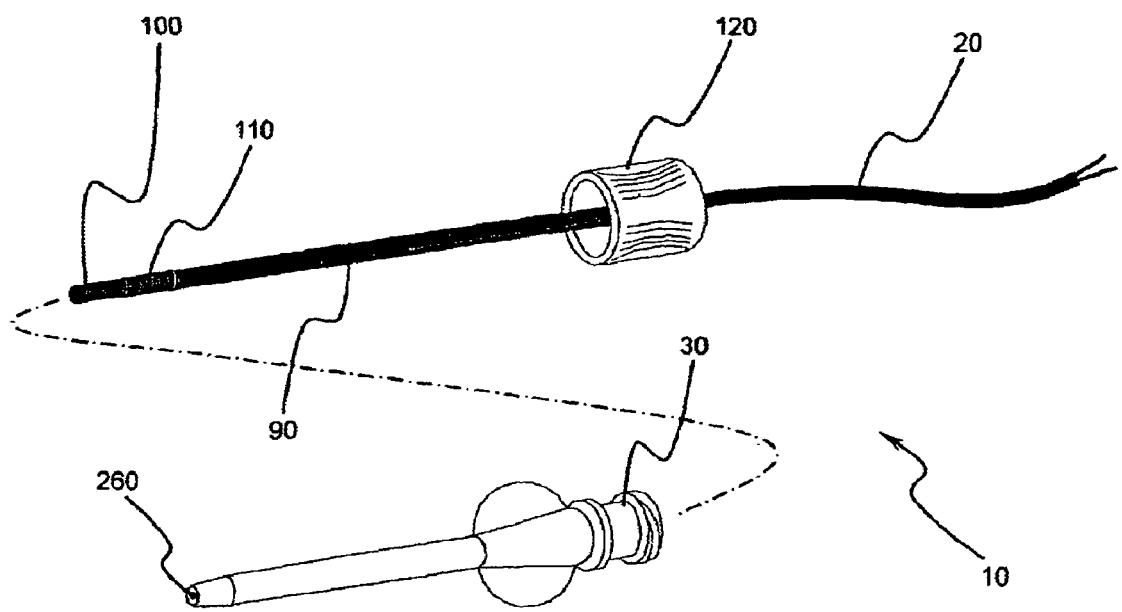
FIG. 2A is a perspective side view in elevation of a first implantable biosensor according to the present invention.
Figure 2B:
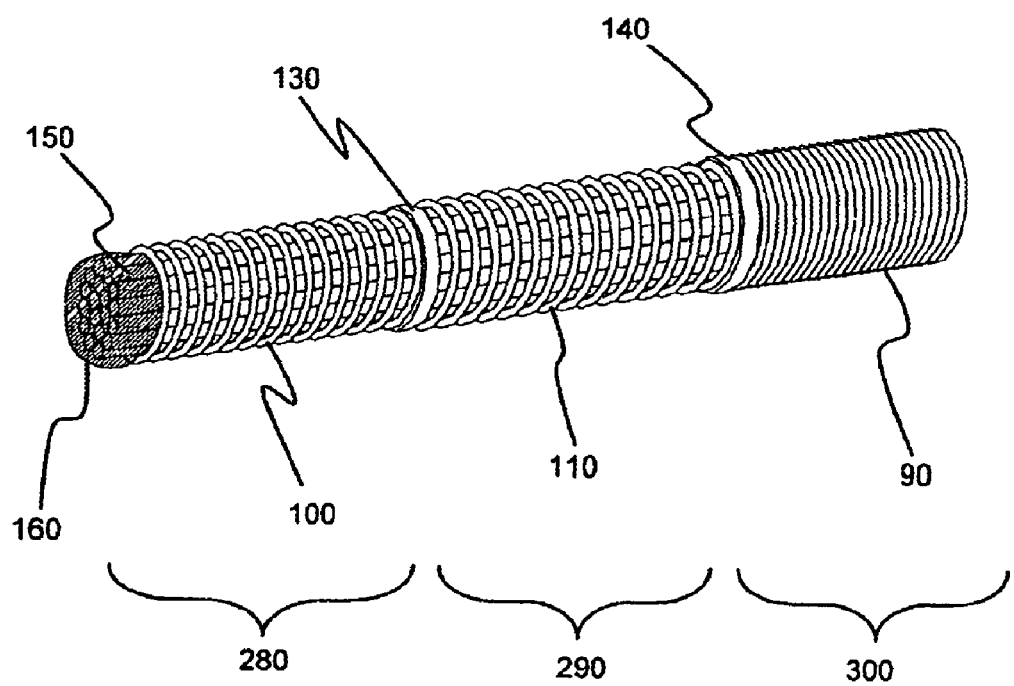
FIG. 2B is an enlarged perspective view in elevation of a probe portion of the implantable biosensor illustrated in FIG. 2A.
Figure 2C:
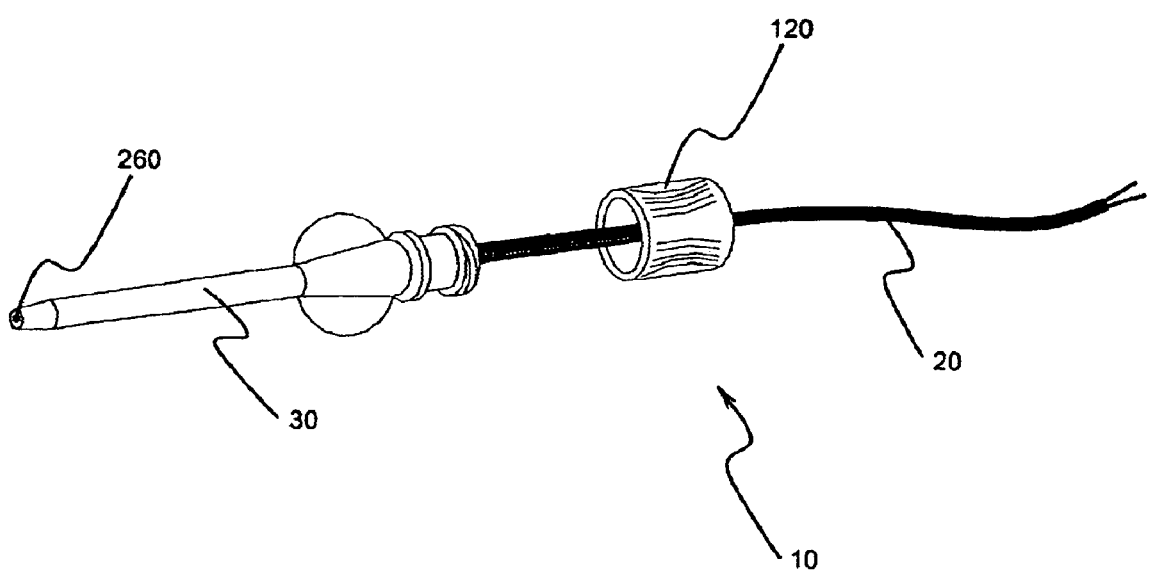
FIG. 2C is a perspective side view in elevation of the implantable biosensor of FIG. 2A, in a partially assembled configuration.

The biosensor 10, as set forth in FIGS. 2A–2D, includes a sensor shaft 90 with sensor cable 20 extending therefrom, a working electrode 100, a reference electrode 110 and a hub 120 for attaching the sensor 10 to the catheter 30. With reference to FIG. 2B, the working electrode 100 and reference electrode 110 are adjacent a first dielectric spacer 130. The reference electrode 110 and sensor shaft 90 are adjacent a second dielectric spacer 140. A filament core 150 is visible in FIG. 2B through a polymer cap 160. The dielectric spacers 130, 140 provide one arrangement of structure operable to prevent the two electrodes from shorting together through a direct physical contact between the electrodes.

Figure 3:
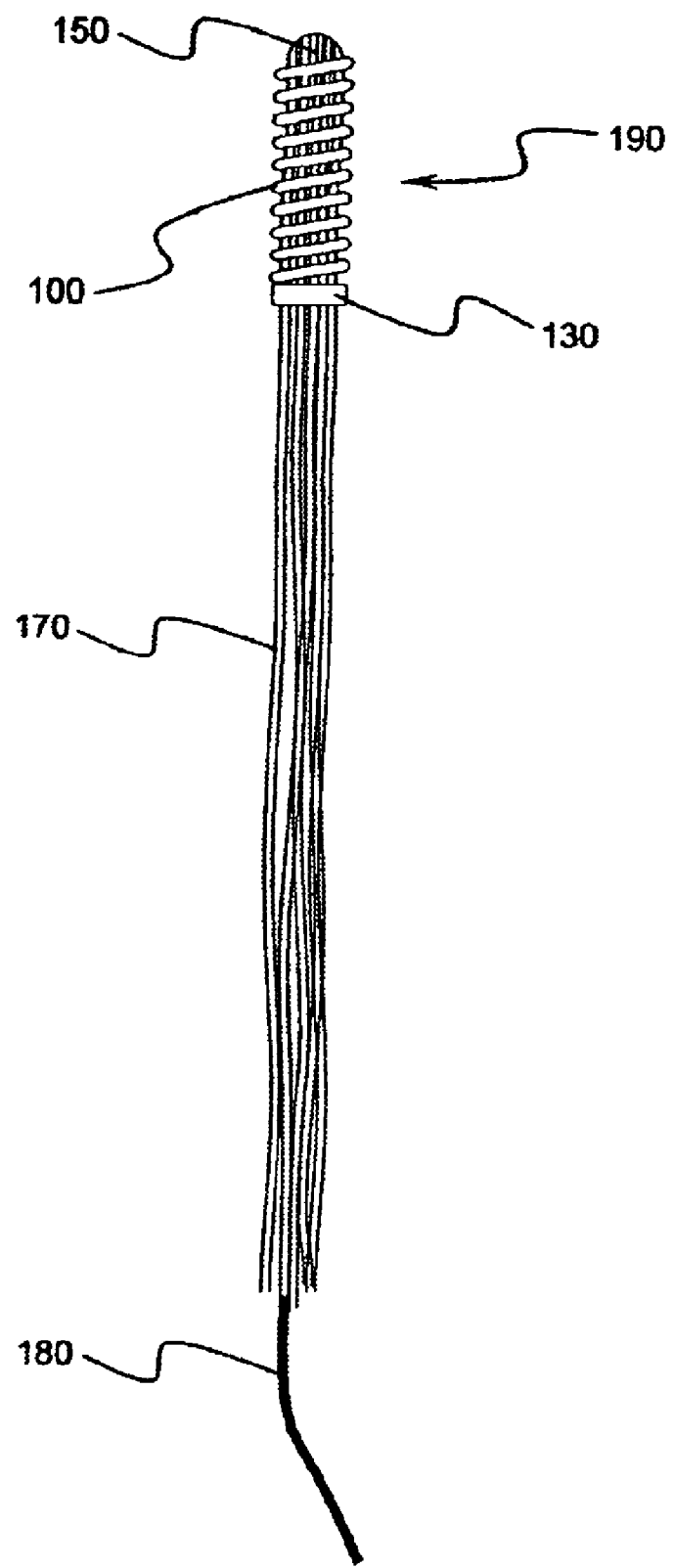
FIG. 3 is a side view illustrating a stage of construction of a probe portion of the implantable biosensor of the invention.

The filament core 150 may include any of a variety of suitable materials, such as: polymeric, ceramic, or flexible metallic materials that can sometimes be insulated. One currently preferred filament core 150, as illustrated in FIG. 3 at an intermediate stage of construction of a biosensor 10, includes a plurality of filamentous fibers 170 of a polymeric material bundled in substantial axial alignment with respect to each other. Filaments 170 forming an exemplary core 150 may be formed from natural or synthetic fibers, and may have round, rectangular, uniform, or even irregular cross-sections. A desirable core material will have sufficient tensile strength to aid in extraction of biosensor elements entrained thereon.

A desirable flexible core 150 forms a biosensor 10 having enhanced transverse flexibility operable to reduce irritation at the installation location in a subject compared to rigid needle-type biosensors. A core 150 desirably is structured and arranged in a multistrand configuration to increase transverse flexibility of biosensor 10. A multistrand core provides a plurality of strands, each strand having a significantly reduced cross-section and bending stiffness compared to a solid cross-section replaced by that core. A plurality of such strands 170 in combination can form a transversely flexible probe 10. For purpose of this disclosure, a solid Copper needle having a diameter of about 25 gage is regarded as being transversely rigid.

Figure 4:
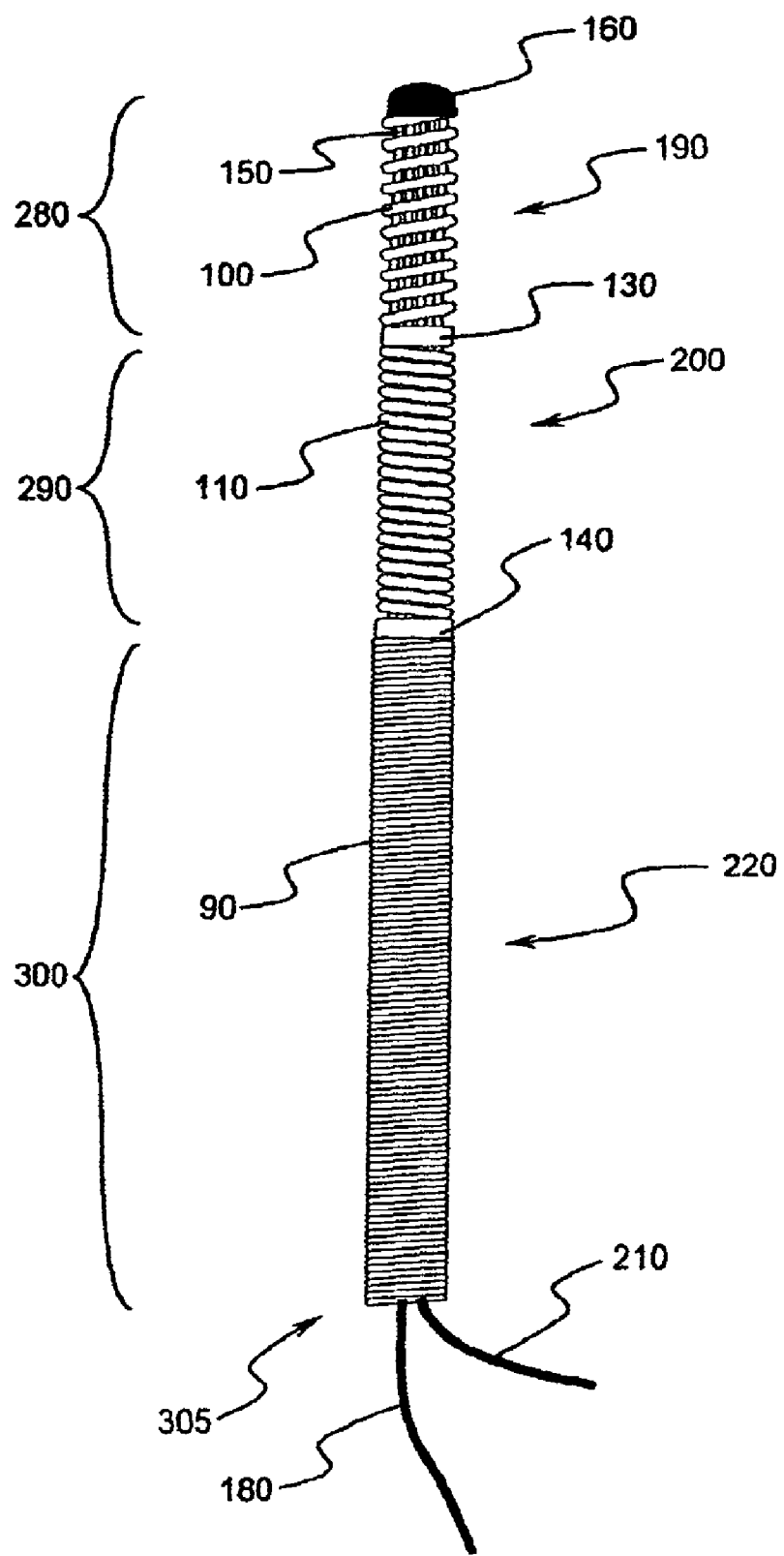
FIG. 4 is a side view of an assembled but uncoated miniature probe portion of the biosensor of the invention.

With reference to FIGS. 3 and 4, working electrode lead 180 provides structure that forms a conductive path that extends from the working electrode 100 for electric communication through the sensor cable 20 (see, FIG. 1). The conductive path can be disposed among the fibers 170, and extends axially along the sensor shaft 90. The working electrode 100 of biosensor 10 is typically formed of platinum, or a platinum compound, and desirably circumscribes the filament core 150 in the form of continuous working coils, generally 190. One operable conductive path is formed by a proximally directed axial extension of a wire formed at its distal end into electrode 100.

The reference electrode 110 in FIG. 4 preferably is formed from a chlorided silver substrate. A reference electrode 110 typically extends axially along a portion of the filament core 150 and desirably circumscribes the core 150 in the form of continuous reference coils, generally 200. A reference wire lead 210 forms a conductive path that extends from the coils 200 of reference electrode 110 for electric communication through the sensor cable 20. An exemplary conductive path can be formed from a proximally extending portion of wire 210 forming the electrode 110. The conductive path can be insulated, and/or disposed among the fibers 170. Both the working wire lead 180 and the reference wire lead 210 are typically available for termination to a distal end of the sensor cable 20 at a hub 120. An extension to leads 180 and 210 may effectively continue from electrical contacts, generally located in association with the hub, to extend along cable 20 and provide electrical contacts at a proximal end of cable 20.

The sensor shaft 90, in certain embodiments, is formed as a cylinder about the core 150. One workable cylinder may, at least in part, be formed of small diameter stainless steel wire. A shaft 90 may be arranged, as illustrated, to circumferentially circumscribe the filament core 150 in the form of continuous body coils, generally 220. Generally, wire used to form coils 190, 200, and 220 has a diameter between about 0.001 and 0.005 inches, with about 0.002 inches being currently preferred. The configuration of coils 190, 200, and 220 desirably lends additional axial compressive load carrying capability to the fibers 170 of the biosensor 10 while maintaining the lateral flexibility of the highly flexible, sometimes even flaccid, fibers 170, thereby reducing a tendency toward scarring in surrounding tissue when implanted.

While the illustrations generally depict electrodes and sensor shafts that are substantially cylindrical, such is not a strict requirement. For instance, a workable core can be formed having a triangular, square, rectangular, or even other alternative shaped, cross-section. An electrode or shaft reinforcement can be wound around such core to form a tube with a cross-section substantially conforming to that of the core. In another example, a reinforcing electrode can be applied to a core having such a non-circular cross-section by way of a coating, printing, vapor deposition, or other procedure, to form a tubular electrode that may be characterized as providing some "effective" inner and outer diameters. Furthermore, in some cases, a shaft reinforcement can be formed from a shrink-fit tubing that substantially conforms to an underlying core profile.

The coils 190, 200, and 220 may be relatively less closely wound (with respect to an axial spacing, or pitch, between centerlines of adjacent coils) about the fibers 170 in certain configurations than embodiments illustrated in this disclosure. However, an increase in the relative closeness of the coils 190 and 200 results in an increase in reactive surface area for the respective electrodes 100, 110, thus enhancing sensitivity and accuracy of readings obtained from a biosensor 10. Adjacent coils 220 can be placed abutting one another (with an axial spacing, or pitch, between centerlines of adjacent coils of one coil-wire diameter) to maximize axial load carrying capabilities of a shaft 90, while still retaining a significant increase in transverse flexibility, compared to a rigid solid shaft.

Construction of a sensor 10, including coils 190, 200, 220 as illustrated, generally enhances the sensor's flexibility and resistance to damage. Transverse flexibility is greatly increased over a comparable solid cross-section, because the load path is changed. Both a solid shaft and a cylinder have a cross-section that carries a bending-induced load along an uninterrupted, axially directed load path as axial tension and axial compression stress. Coils provide an axially interrupted load path along a length of the electrode (or shaft 90). Coil structure cannot carry bending loads in the same way an uninterrupted surface can. Under transverse bending of an illustrated sensor 10, the coils displace in a shear mode, and carry loads as torsion and bending loading in the coil elements, but the bending load path and effective displacements are entirely different than those in a solid shaft. For example, the bending of a coil element is essentially orthogonal to the bending in the equivalent uninterrupted surface. The stress induced in the coil element is therefore significantly lower (potentially by orders of magnitude) than the stress induced in the comparable solid cross-section. A coil arrangement therefore resists breaking-off of electrode portions inside a subject, and reduces irritation at the implantation interface.

An axially interrupted electrode can be formed other than as a coil structure. For example, a cylinder can be made to provide circumferential relief, or radially directed cuts, in an overlapping finger pattern. Such relief can be laser etched from a continuous cylinder. Alternatively, such pattern can be printed, or etched. The relief also provides a radial component to the electrode surface, thereby potentially increasing the available reactive surface area of the electrode.

Core 150 and its associated cap 160 work in harmony further to resist leaving any broken-off portions of electrode, such as working electrode 100, behind in a subject when a biosensor 10 is removed from a subject's tissue. Cap 160 desirably is operable as a stopper forming an interference to resist extraction of core 150 from within an electrode. That is, the stopper functions to hold an electrode (such as electrode 100) at a distal tip end 310, placing the electrode 100 into compression during withdrawal of a sensor 10. A cap 160 desirably provides structure sized larger than an inside diameter of an electrode. Therefore, the cap 160 forms an interference with the electrode to resist separation of the electrode from the core 150. Certain embodiments of cap 160 may adhere an electrode, or a portion of an electrode, directly to a core 150. It is within contemplation for a cap 160 to be formed by melting a distal portion of a core 150. The core 150 desirably provides a strand of material having sufficient tensile strength to overcome resistance due to adhesion between body tissue and portions of a biosensor 10. Therefore core 150 and cap 160 are relied upon for extraction of the biosensor 10.

Figure 5:
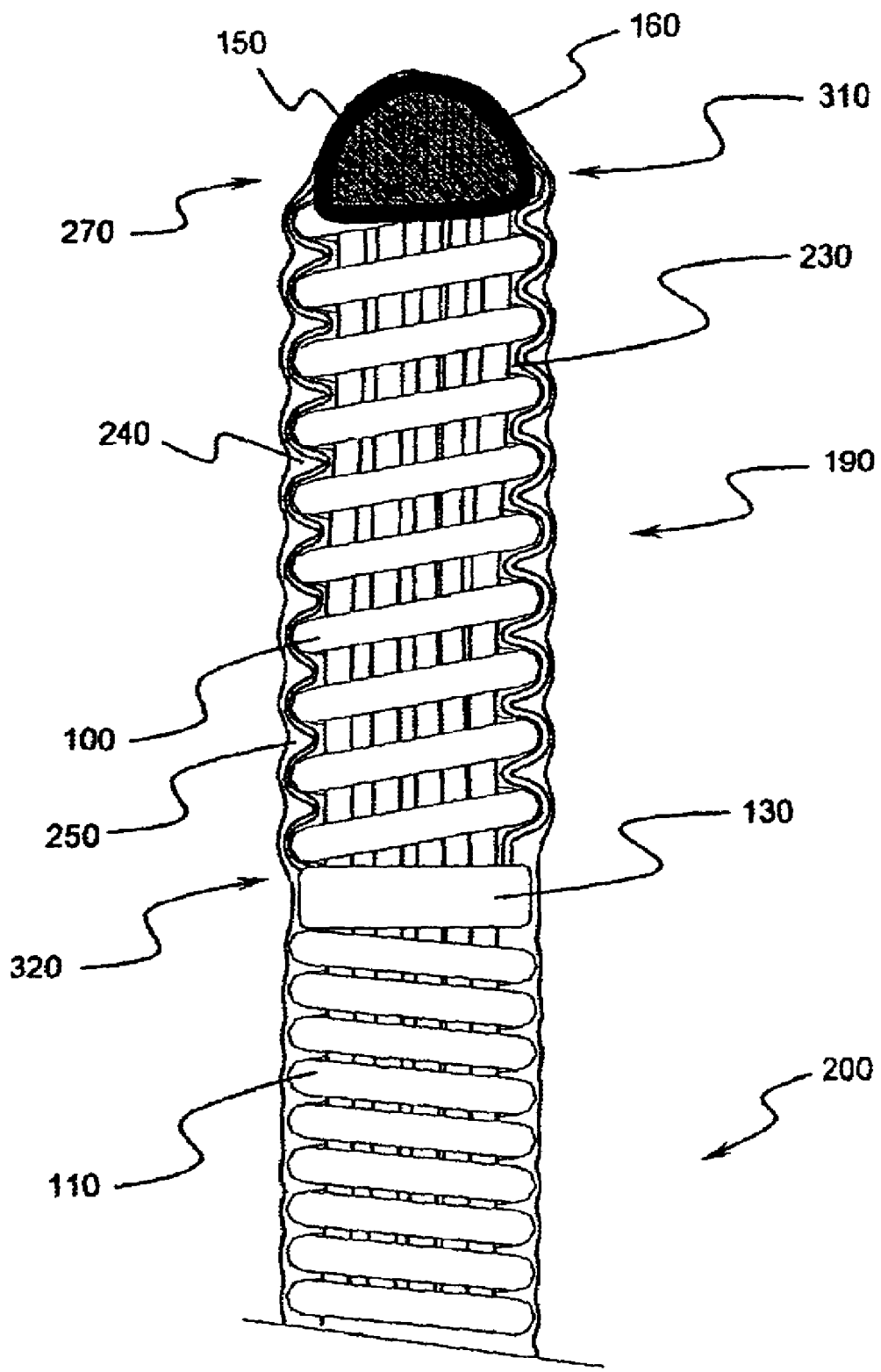
FIG. 5 is an enlarged cross-sectional side view of a miniature, flexible probe portion of the implantable biosensor.
Figure 6A:
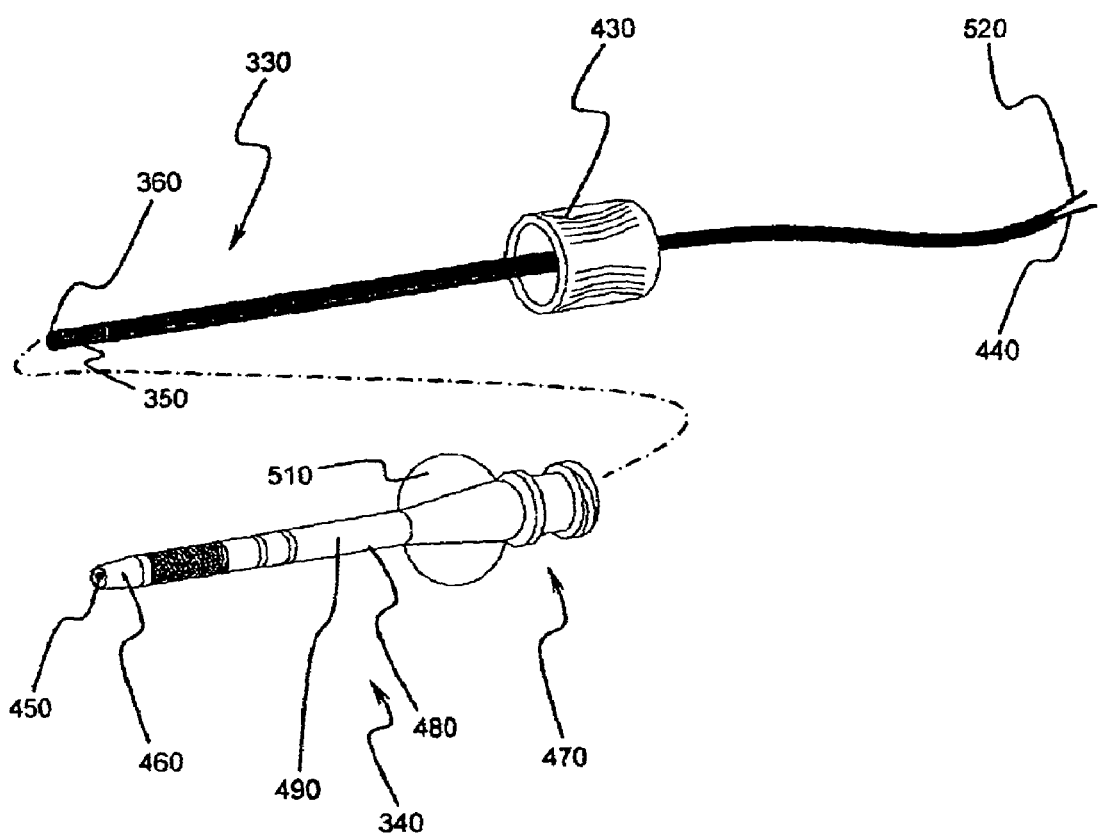
FIG. 6A is a perspective side view in elevation of a second implantable biosensor according to the present invention.

The electrodes 100 and 110 of the biosensor 10 in a preferred embodiment are illustrated in an enlarged view in FIG. 5 to illustrate three layers of membranes. An inner exclusion membrane 230 is depicted as surrounding and being adjacent to the working electrode 100. The inner exclusion membrane 230, preferably formed of polysulfone or sulfonated polyethersulfone, serves to reduce the sensor artifact that is caused by non-endogenous electroactive molecules, thus excluding interfering compounds such as ascorbic acid and acetaminophen. A middle enzymatic membrane 240 surrounds the inner exclusion membrane 230. The middle enzymatic membrane 240 includes immobilized glucose oxidase enzyme that converts glucose to hydrogen peroxide, to generate a current. An outer polymer membrane 250 surrounds the middle enzymatic membrane 240, as well as the reference electrode 110, to restrict diffusion of glucose while allowing the free passage of oxygen. This outer membrane 250 may be formed of various polymers. One preferred embodiment of an outer membrane 250 is formed of polyurethane. A careful approach to material selection for the membrane layers, 230, 240, and 250 facilitates correction of the non-linear diffusion of glucose and reduces errors resulting from interfering electroactive species.

It can be appreciated that the introducer catheter 30, typically used in conjunction with a preferred embodiment 10, provides access from outside the body (not shown) to the tissue just under the skin layer (not shown). With reference to FIG. 2A, the biosensor 10 is inserted into and through a lumen 260 of the catheter 30 to a point at which the polymer cap 160, working electrode 100 and reference electrode 110 of the biosensor 10 protrude beyond and outside the catheter 30 lumen 260. Such placement allows the working electrode 100 and reference electrode 110 to be in communication with the surrounding tissue (not illustrated).

Figure 2D:
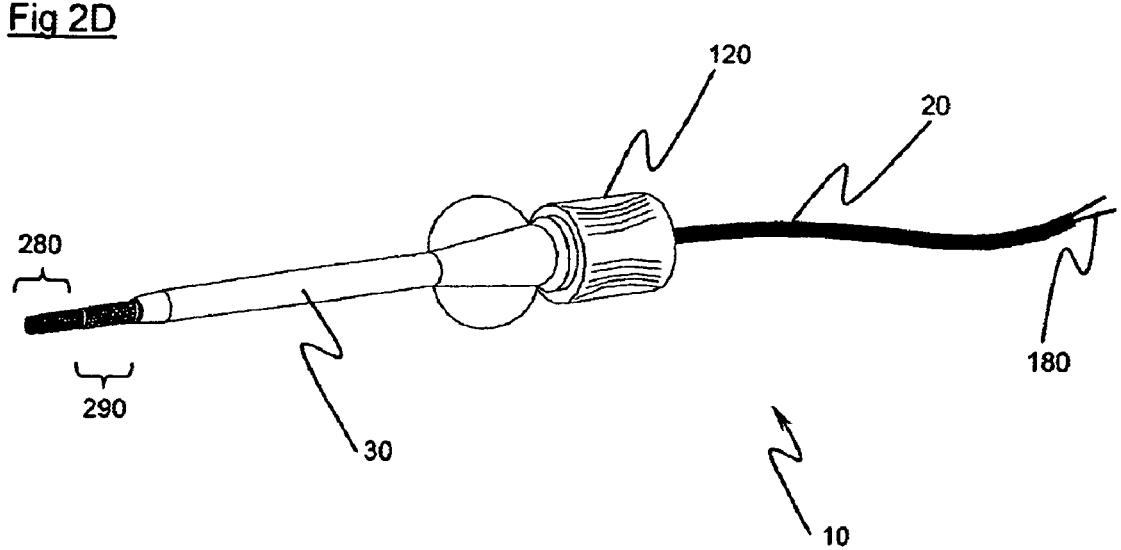
FIG. 2D is a perspective side view in elevation of the implantable biosensor of FIG. 2A, in an assembled configuration.

With reference to FIGS. 2B and 5, polymer cap 160, located at a head portion 270 of the biosensor 10, provides a conformal material that coats the fibers 170 extending beyond the working electrode 100 and adheres the fiber filaments 170 into the unified filament cap 150. The working electrode 100, as illustrated, extends along a leading portion, generally 280, of the biosensor 10. As further illustrated, the reference electrode 110 extends along the trailing portion 290. The leading portion 280 and trailing portion 290, as best illustrated in FIG. 2D, extend beyond the lumen 260 of the introducer catheter 30 when introduced into a subject. The sensor shaft 90 may include a tail portion 300 along which the body coils 220 may be located (see, FIG. 4).

As illustrated in FIG. 5, working electrode 100 includes a distal tip end, generally 310, and a proximal tip end, generally 320. The distal tip end 310, as illustrated, is associated with the filament core 150 at or near the head portion 270. The proximal tip end 320 is associated with the filament core 150 at or near the trailing portion 290 or tail portion 300 depending upon the configuration. In one configuration, a reference electrode 110 is separate from a needle-probe portion of a biosensor. In another configuration and as illustrated in FIG. 5, a reference electrode 110 is included on the biosensor 10 probe.

The preferred embodiment 10 illustrates the working electrode 100 as being structured in the form of coils. However, it is only necessary that the working electrode 100 be in length substantially not less in length than the leading portion 280 when the leading portion 280 is laterally deflected to a maximum extent. Such a limitation is operable to resist separation of an electrically conductive path from the electrode due to bending of the biosensor. Correspondingly, whereas in a preferred embodiment the reference electrode 110 is illustrated as being in the form of coils, in essence a working electrode 110 may be in length substantially not less than the trailing portion 290 when the trailing portion 290 is laterally deflected to a maximum extent.

FIGS. 6A–6D illustrate an alternative preferred embodiment of a biosensor, generally indicated at 330, including an introducer catheter, generally indicated at 340. The biosensor 330 includes a working electrode, generally 350, typically corresponding in function, materials, location and other general characteristics with the working electrode 100. The biosensor 330 further includes a polymer cap 360, filament core 370, working coils 380, dielectric spacer 390, head portion, generally 400; leading portion 410, tail portion 420, hub 430, working electrode lead 440, and body coils 445. Biosensor 330 generally includes membranes and is structured to provide characteristics and features that in turn generally correspond to those of the biosensor embodiment 10.

The sensor catheter 340, like the introducer catheter 30, includes a lumen that may be thought of as an interior cannula lumen 450. Furthermore, the illustrated sensor catheter 340 presents an advanced end 460 designed for subcutaneous or other intra-tissue placement, an opposite end, generally 470, and a cannula wall 480 defining the interior cannula lumen 450 and comprising an exterior surface 490. The exterior surface 490 and the interior cannula lumen 450 extend between the advanced end 460 and the opposite end 470. In the biosensor embodiment 330, a reference electrode 500 is associated with the exterior surface 490 of catheter 340 in the vicinity of the advanced end 460. Electrode 500 may take other forms, such as a film, band, etching, printed or imprinted layer, or a shell or coating. The interior cannula lumen 450 is of sufficient cross-sectional diameter to pass the sensor 330. The advanced end 460 and exterior surface 490 of the sensor catheter 340 are structured and arranged to enable access of the advanced end 460 into and through subcutaneous or other subject tissue.

The opposite end 470 generally includes one or more surfaces 510 useful for adhesively fixing the sensor catheter 340 to the skin. The hub 430 may be anchored to the opposite end 470 of the sensor catheter 340. The opposite end 470 may be further structured and arranged to engage the hub 430, upon advancement of the sensor 330 through the interior cannula lumen 450 sufficiently far, so that the alternative working electrode 350 reaches a position extending beyond the advanced end 460. Upon achievement of such a position, a reference wire lead 520 associated with the hub 430 may be brought into register with the reference electrode 500 carried by the catheter 340.

Glucose ("Glu") in a somewhat restricted manner, and Oxygen ("$O_2$") comparatively freely, diffuse from the interstitial tissues of the subject through the outer polymer membrane 250 (see FIG. 5) and, in the presence of the glucose oxidase ("GOx") of the middle enzymatic membrane 240, produce gluconic acid ("GluA") and hydrogen peroxide ("$H_2O_2$"). The $H_2O_2$, upon interaction with the platinum ("Pt") working electrode 100, which is typically polarized at approximately 0.7 volts, creates a current which travels up the working wire lead 180 for processing through the sensor module 40. A differential signal is generally measured between the working electrode 100 and the reference electrode 110 at the sensor module 40, and successively transmitted to the SDU 60 and ultimately the computer 80.

In the manufacture of a biosensor 10, a plurality of filamentous fibers 170 of the filament core 150 are axially aligned in a bundle and bonded to form the polymer cap 160. The wire material of a working electrode 100 can be manually or mechanically wrapped around the core 150 beginning at the head portion 270 and continuing proximally across the leading portion 280 to form the working coils 190 (see FIGS. 4 and 5). An exemplary working electrode 100 is somewhat cylindrical, about 0.60 inches in axial length and about 0.015 inches in maximum outside diameter. It is currently preferred to form an electrode, such as a working electrode 100, from a wire wound on a spiral path.

If the biosensor includes a reference electrode 110 adjacent to, but apart from, the working electrode 100, the reference electrode 110 can likewise be manually or mechanically wrapped around the core 150 and working wire lead 180. Reference electrode 110 is structured to occupy a desired axial distance and desirably forms reference coils 200 electrically communicating with the reference wire lead 210. Reference wire lead 210 and the working wire lead 180 extend proximally among the fibers 170. Body coils 220 are then similarly wrapped around the core 150 and leads 180 and 210, terminating at a proximal end, generally indicated at 305.

A core may also be threaded through preformed electrodes and dielectric spacers. Certain preferred polymer cores can be heated and drawn slightly at a distal portion to form an operable needle to assist in threading the electrodes. In embodiments manufactured by threading one or more premanufactured electrodes, a conductive path from the respective electrode(s) is/are generally insulated prior to the threading assembly step. The conductive path typically includes a proximally protruding portion of the wire forming a coiled electrode. Such proximally directed wire desirably is disposed among strands of a core for additional insulation.

The working electrode 100 is next manually or mechanically dipped in a vertical orientation into at least one coating of 5% polyethersulfone in the solvent DMAC to form the inner exclusion membrane 230, and dried to ensure solidification of the coating. Of course, while reference is made in this disclosure to dipping, it is to be realized that other procedures operable to apply a coating (e.g., brushing, spraying, vapor deposition, and the like), are intended to be encompassed by such language. Successive coatings may be desirable and accomplished by repeating the application process.

The working electrode 100 and core 150 are then manually or mechanically dipped in a vertical orientation into at least one coating of 1% glucose oxidase, 0.6% albumin and 0.5% glutaraldehyde in water to form the middle enzymatic membrane 240, and dried to ensure solidification of the coating. As with the inner exclusion membrane 230, successive coatings may be desirable and accomplished by repeating the foregoing process. In certain embodiments, the electrode is assembled onto a filament core 150 before the step of applying glucose oxidase. In that case, the glucose oxidase can fill in any spaces between the core fibers 170 to increase the volume of glucose oxidase associated with the electrode. The increased volume of glucose oxidase provides enhanced sensor stability and shelf life.

Next, in biosensor configurations such as embodiment 10, having the working electrode 100 and reference electrode 110 being positioned adjacent but separate from each other on the filament core 150, both the working and reference electrodes 100 and 110 are manually or mechanically dipped in a vertical orientation into at least one coating of 5% polyurethane in the solvent tetrahydrofuran to form the outer polymer membrane 250, and dried to ensure solidification of the coating. Again, successive coatings may be desirable and accomplished by repeating the foregoing process. Successive coatings contemplate use of an approximately 5% solution in a solvent such as, for example, tetrahydrofuran or methylene chloride, to allow for solvent drying from liquid to gel to jelly to a tightly bound conformal coating. The coating materials and respective number of layers are selected to balance response time, electrical insulation, biocompatibility and diffusive properties. For example, a thicker layer increases response time but provides better insulation. To enhance biocompatibility, the outermost surface of the final layer can be made microscopically rough by phase inversion polymerization, i.e., by immediately dipping the last layer in water to allow the miscible solvent to be largely rinsed away soon after the first of the fibers comprising the 5% solution have begun to bond with the second to last layer. Such a procedure typically results in a surface including projecting particles that are sized between about 5 and 50 microns.

If the biosensor is structured to include coterminous wrapping of both the working and reference electrodes 100, 110, then the sequence of the foregoing method of manufacturing would be altered by, prior to coiling, applying the inner exclusion membrane 230, the middle enzymatic membrane 240 and a preliminary outer polymer membrane 250 coating to the portion of the working electrode 100 to be coiled, then coiling both the coated working electrode 100 and the reference electrode 110 over a portion of the filament core 150 comparable in length to both working and reference coils 190, 200 when adjacent but separate, and finally coating both coterminous coiled electrodes 100, 110 as desired.

The system, apparatus and method of the present invention provide distinct advantages over prior implantable biosensors. Thus, reference herein to specific details of the illustrated or other preferred embodiments is by way of example and not intended to limit the scope of the appended claims. It will be apparent to those skilled in the art that modifications of the basic illustrated embodiments may be made without departing from the spirit and scope of the invention as recited by the claims.

What is claimed is:

1. An implantable needle-type biosensor wherein an electric signal is produced between first and second electrical contacts responsive to an electrochemical reaction in a body, said biosensor comprising:
    an elongate core comprising a plurality of axially oriented fibers, said elongate core having a distal end and a proximal end, said distal end being spaced apart in an axial direction from said proximal end;
    a working electrode associated with said distal end;
    a reference electrode spaced apart from said working electrode;
    structure adapted to resist direct physical contact between said working electrode and said reference electrode;
    a first electrically conductive path between said working electrode and said first electrical contact; and
    a second electrically conductive path between said reference electrode and said second electrical contact, wherein said distal end of said core carries a plug structured to resist extraction of said core from within a portion of said working electrode as said biosensor is removed from said body, to resist leaving a detached portion of said working electrode in the body.

2. The implantable needle-type biosensor of claim 1, wherein said working electrode comprises a metal element formed as a wrap about a portion of said core.

3. The implantable needle-type biosensor of claim 1, wherein said working electrode comprises a length of a first wire arranged to circumscribe a plurality of revolutions about said core.

4. The implantable needle-type biosensor of claim 3, wherein said first wire's diameter is between about 0.001 and about 0.005 inches.

5. The implantable needle-type biosensor of claim 1, wherein said working electrode comprises a first wire arranged to form a spiral path.

6. The implantable needle-type biosensor of claim 5, wherein said spiral path has an axial pitch spacing, between centerlines of a pair of adjacent wire wraps, sized between about one and about four diameters of said first wire.

7. The implantable needle-type biosensor of claim 1, wherein said working electrode is arranged in harmony with said core to form a reinforced core operable to carry an axial compression load permitting insertion of a distal tip of said biosensor through an introducer catheter for placement of said working electrode into intimate contact with tissue of the body.

8. The implantable needle-type biosensor of claim 1, wherein said reference electrode and said working electrode are both arranged for disposition in intimate contact with tissues of a subject.

9. The implantable needle-type biosensor of claim 1, wherein said plug comprises a polymer coating.

10. The implantable needle-type biosensor of claim 1, wherein:
said plug comprises an enlargement in a cross-section comprising material of said core, said enlargement being disposed distal to said working electrode.

11. The implantable needle-type biosensor of claim 1, wherein said plug comprises a dielectric adhesive.

12. The implantable needle-type biosensor of claim 1, wherein said reference electrode is associated with said distal end and comprises a length of a second wire formed as a wrap about a portion of said core.

13. The implantable needle-type biosensor of claim 12, further comprising:
a dielectric spacer interposed between said working electrode and said reference electrode to resist direct physical contact therebetween.

14. The implantable needle-type biosensor of claim 1, further comprising:
a sensor shaft disposed between said working electrode and a hub, said shaft comprising a cylinder disposed circumferentially about an axial length of said core proximal to said working electrode.

15. The implantable needle-type biosensor of claim 1, wherein said core comprises an electrically nonconductive material.

16. The implantable needle-type biosensor of claim 15, wherein said core comprises a polymer material.

17. The implantable needle-type biosensor of claim 1, wherein said working electrode comprises an exterior coating of a negatively charged polymer.

18. The implantable needle-type biosensor of claim 17, wherein said negatively charged polymer comprises sulfonated polyethersulfone.

19. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end;
a working electrode associated with said distal end;
a reference electrode spaced apart from said working electrode;
structure adapted to resist direct physical contact between said working electrode and said reference electrode;
a first electrically conductive path between said working electrode and said first electrical contact;
a second electrically conductive path between said reference electrode and said second electrical contact; and
a sensor shaft disposed between said working electrode and a hub, said shaft comprising a cylinder disposed circumferentially about an axial length of said core proximal to said working electrode, wherein said cylinder comprises a plurality of circumferential wrappings of a component wire having a smaller diameter than a diameter of said cylinder, said wrappings being closely spaced in an axial direction along an axis of said cylinder whereby to enable said shaft to carry an axial compression load effective to install said biosensor through an introducer cannula and into a body.

20. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end:
a working electrode associated with said distal end;
a reference electrode spaced apart from said working electrode;
structure adapted to resist direct physical contact between said working electrode and said reference electrode;
a first electrically conductive path between said working electrode and said first electrical contact;
a second electrically conductive path between said reference electrode and said second electrical contact;
a sensor shaft disposed between said working electrode and a hub, said shaft comprising a cylinder disposed circumferentially about an axial length of said core proximal to said working electrode; and
a dielectric spacer disposed at a distal end of said cylinder effective to resist direct physical contact between said shaft and a said electrode.

21. The implantable needle-type biosensor of claim 20, wherein said dielectric spacer comprises a droplet of dielectric adhesive bonded to a portion of said core.

22. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end;
a working electrode associated with said distal end;
a reference electrode spaced apart from said working electrode;
structure adapted to resist direct physical contact between said working electrode and said reference electrode;
a first electrically conductive path between said working electrode and said first electrical contact;
a second electrically conductive path between said reference electrode and said second electrical contact;
a sensor shaft disposed between said working electrode and a hub, said shaft comprising a cylinder disposed circumferentially about an axial length of said core proximal to said working electrode; and
a sensor cable affixed to structure associated with said hub, said sensor cable comprising first and second wires, a first end of said first and second wires being arranged to make respective electrical connections with said first and second electrical contacts, a second end of said first and second wires being affixed to a sensor module operable to impose a conditioning signal on said biosensor.

23. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end;
a working electrode associated with said distal end;
a reference electrode spaced apart from said working electrode, wherein said reference electrode is associated with said distal end and comprises a length of a second wire formed as a wrap about a portion of said core;

structure adapted to resist direct physical contact between said working electrode and said reference electrode;
a first electrically conductive path between said working electrode and said first electrical contact;
a second electrically conductive path between said reference electrode and said second electrical contact; and
a dielectric spacer interposed between said working electrode and said reference electrode to resist direct physical contact therebetween, wherein said dielectric spacer comprises a droplet of dielectric adhesive bonded to a portion of said core, said droplet being arranged effectively to resist extraction of said core from within a portion of said reference electrode as said biosensor is removed from the body, to resist leaving a detached portion of said reference electrode in the body.

24. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end, wherein said core comprises a plurality of spaces between said fibers operable to carry glucose oxidase to enhance a volume of said glucose oxidase associated with said working electrode;
a working electrode associated with said distal end;
a reference electrode spaced apart from said working electrode;
structure adapted to resist direct physical contact between said working electrode and said reference electrode;
a first electrically conductive path between said working electrode and said first electrical contact; and
a second electrically conductive path between said reference electrode and said second electrical contact.

25. An implantable needle-type biosensor wherein an electric signal is produced between first and second electrical contacts responsive to an electrochemical reaction in a body, said biosensor comprising:
an elongate core comprising a plurality of axially oriented fibers, said elongate core having a distal end and a proximal end, said distal end being spaced apart in an axial direction from said proximal end;
a working electrode associated with said distal end, wherein said working electrode comprises an exterior coating of a negatively charged polymer, and wherein an outer surface of said coating is arranged to provide a microscopically rough surface, comprising projecting particles sized between about 5 and 50 microns, to enhance biocompatibility of said biosensor with the body;
a reference electrode spaced apart from said working electrode;
structure adapted to resist direct physical contact between said working electrode and said reference electrode;
a first electrically conductive path between said working electrode and said first electrical contact; and
a second electrically conductive path between said reference electrode and said second electrical contact.

26. An implantable needle-type biosensor comprising:
an introducer cannula with a lumen extending axially between proximal and distal ends, said proximal end carrying affixing structure adapted to resist motion of said proximal end relative to a skin surface of a subject and further carrying holding structure arranged to receive cooperating held structure of a probe;
said probe comprising an elongate substantially nonconductive core having a distal end and a proximal end, said distal end being spaced apart axially from said proximal end, said proximal end being associated with a hub comprising said held structure;
a working electrode associated with said distal end of said probe, said working electrode comprising a metallic element formed to circumscribe said core;
a reference electrode supported by structure adapted to resist direct physical contact between said working electrode and said reference electrode;
a first electrically conductive path between said working electrode and said hub; and
a second electrically conductive path between said reference electrode and said hub.

27. The implantable biosensor of claim 26, wherein:
said reference and said working electrodes are both arranged for disposition in intimate contact with tissue of a subject.

28. The implantable needle-type biosensor of claim 26, wherein:
said metallic element is arranged to provide electrode having a length and an axially interrupted load path between first and second ends, a maximum equivalent outside diameter, a minimum equivalent inside diameter, and a surface texture disposed between said first and second ends that has a radially oriented component, said electrode having a larger reactive surface area and a lower bending stiffness compared to a hollow cylinder structured from an equivalent material and having equivalent maximum outside and minimum inside diameters.

29. The implantable needle-type biosensor of claim 26, wherein said metallic element comprises a first wire formed into a spiral with a portion of said core being disposed substantially coaxial with an axis of said spiral.

30. The implantable needle-type biosensor of claim 29, wherein said spiral has an axial spacing, between centerlines of adjacent wraps of said first wire, sized between about one and about four diameters of said first wire.

31. The implantable needle-type biosensor of claim 29, wherein a diameter of said first wire is between about 0.001 and about 0.005 inches.

32. The implantable needle-type biosensor of claim 26, wherein said core comprises a polymer.

33. The implantable needle-type biosensor of claim 26, further comprising:
a plug carried by said core and structured to resist extraction of said core from within a portion of said working electrode as said probe is removed from a body, whereby to resist leaving a detached portion of said working electrode in the body.

34. The implantable needle-type biosensor of claim 26, wherein said core comprises a plurality of axially oriented fibers arranged to provide spaces between said fibers operable to carry glucose oxidase whereby to enhance a volume of said glucose oxidase associated with said working electrode.

35. The implantable needle-type biosensor of claim 26, further comprising:
a sensor shaft disposed between said working electrode and said hub, said shaft comprising a cylinder disposed circumferentially about an axial length of said core proximal to said working electrode.

36. The implantable needle-type biosensor of claim 35, wherein said cylinder comprises a plurality of circumferential wrappings of a component wire having a smaller diameter than a diameter of said cylinder, said wrappings being closely spaced along an axis of said cylinder whereby to enable said shaft to carry an axial compression load effective to install said biosensor through said introducer cannula and into a body.

37. The implantable needle-type biosensor of claim 35, further comprising:
a dielectric spacer disposed at a distal end of said cylinder effective to resist direct physical contact between said shaft and a said electrode.

38. The implantable needle-type biosensor of claim 26, wherein:
said reference electrode is associated with said distal end and comprises a second metallic element formed to circumscribe said core; and
a dielectric spacer is interposed between said working electrode and said reference electrode to resist direct physical contact therebetween.

39. The implantable needle-type biosensor of claim 26, wherein said reference electrode is associated with said introducer cannula.

40. The implantable needle-type biosensor of claim 26, wherein said reference electrode is recessed into an exterior surface of said introducer cannula.

41. The implantable needle-type biosensor of claim 26, wherein said reference electrode is structured as a coating on an exterior surface of said cannula.

42. The implantable needle-type biosensor of claim 26, wherein said reference and said working electrodes are both arranged for disposition in intimate contact with tissues of a subject.

43. The implantable needle-type biosensor of claim 42, wherein said working electrode comprises an exterior coating of a negatively charged polymer.

44. The implantable needle-type biosensor of claim 43, wherein said negatively charged polymer comprises sulfonated polyethersulfone.

45. The implantable needle-type biosensor of claim 43, wherein an outer surface of said coating is arranged to provide a microscopically rough surface, comprising protruding particles sized between about 5 and 50 microns, so as to enhance biocompatibility of said biosensor with the body.

46. A method for manufacturing an implantable, needle-type biosensor probe with a transversely flexible first electrode effective to resist irritation at a site of implantation in a subject, the method comprising:
providing a core comprising a first nonconductive material;
disposing a first electrode in a reinforcing path about said core;
disposing structure forming a first electrical conductor between said first electrode and a hub associated with a proximal end of said probe;
disposing structure forming a second electrical conductor between a second electrode and said hub;
applying an electrically insulating material to said structure forming said first electrical conductor extending proximally from said first electrode;
disposing a second wire circumferentially about said core in a spiral reinforcing path operable to enhance an axial compression load carrying capability of said core, to form said second electrode; and
affixing a droplet of dielectric adhesive to said core, said droplet being disposed between said first electrode and said second electrode and operable to resist extraction of said core from retention in said second electrode, whereby to resist leaving a portion of said second electrode inside a subject subsequent to extraction of said probe.

47. The method of claim 46, further comprising the steps of:
wrapping a third wire circumferentially about said core in a spiral reinforcing path operable to enhance an axial load carrying capability of said core, whereby to form a shaft of said probe; and
affixing said hub to a proximal portion of said shaft.

48. The method of claim 47, further comprising the steps of:
applying a solution of 5% polyethersulfone to said first electrode to form an inner exclusion membrane associated with said first electrode;
applying a solution of 1% glucose oxidase, 0.6% albumin and 0.5% glutaraldehyde to said first electrode and a portion of said core to form a middle enzymatic membrane; and
applying a solution of 5% polyurethane to both said first and said second electrodes to form an outer polymer membrane.

49. The method of claim 48, further comprising the step of:
performing a phase inversion polymerization procedure effective microscopically to rough-up an outermost surface of said outer polymer membrane.

50. A method for manufacturing an implantable, needle-type biosensor probe with a transversely flexible first electrode effective to resist irritation at a site of implantation in a subject, the method comprising:
providing a core comprising a first nonconductive material;
disposing a first electrode in a reinforcing path about said core;
disposing structure forming a first electrical conductor between said first electrode and a hub associated with a proximal end of said probe;
disposing structure forming a second electrical conductor between a second electrode and said hub; and
forming a stopper carried by said core, a portion of said stopper being disposed distal to said first electrode and being operable to retain an association between said core and said second electrode whereby to resist leaving a portion of said electrode inside a subject subsequent to removal of said probe.

51. The method of claim 50, further comprising:
forming said first electrode from a first wire, a diameter of said first wire being between about 0.001 and about 0.005 inches; and
disposing said first wire in a spiral path about said core.

52. A method for manufacturing an implantable, needle-type biosensor probe with a transversely flexible first electrode effective to resist irritation at a site of implantation in a subject, the method comprising the steps of:
providing a core comprising a first nonconductive material;
disposing a first electrode in a reinforcing path about said core;
disposing structure forming a first electrical conductor between said first electrode and a hub associated with a proximal end of said probe;
disposing structure forming a second electrical conductor between a second electrode and said hub; and
forming said first electrode as a first cylinder with an axially interrupted load path, said cylinder having a first length between a first end and a second end, a maximum equivalent outside diameter, and a minimum equivalent inside diameter, said first cylinder further comprising a surface texture disposed between said first and second ends that has a radially oriented component whereby to provide a larger reactive surface area and a lower bending stiffness than an uninterrupted second cylinder having an equivalent maximum outside diameter and first length.

* * * * *